United States Patent [19]
Allen

[11] Patent Number: 5,443,528
[45] Date of Patent: Aug. 22, 1995

[54] COIL SPRING PROSTHETIC FOOT

[76] Inventor: Scott Allen, 2286 Harvest La., West Jordan, Utah 84084

[21] Appl. No.: 977,806

[22] Filed: Nov. 17, 1992

[51] Int. Cl.$^6$ .............. A61F 2/66; A61F 2/70
[52] U.S. Cl. .................... 623/52; 623/55; 623/24
[58] Field of Search .......... 623/55, 52, 24, 50, 623/53, 47

[56] References Cited

U.S. PATENT DOCUMENTS

| | | | |
|---|---|---|---|
| 428,839 | 5/1890 | Gault | 623/55 |
| 563,247 | 7/1896 | Andrews . | |
| 597,465 | 1/1898 | Hagen | 623/52 X |
| 942,521 | 12/1909 | Rowley . | |
| 1,071,230 | 8/1913 | Hanger . | |
| 1,289,580 | 12/1918 | Vincenti . | |
| 1,319,471 | 10/1919 | Giebeler-Warke . | |
| 1,424,264 | 8/1922 | Shrodes . | |
| 1,459,564 | 6/1923 | Tracy . | |
| 1,502,593 | 7/1924 | Shrodes | 623/52 |
| 1,617,925 | 2/1927 | Shrodes | 623/52 |
| 2,036,830 | 4/1936 | Rowley . | |
| 2,440,075 | 4/1948 | Campbell | 623/50 |
| 2,443,356 | 7/1948 | Mathis . | |
| 2,453,969 | 11/1948 | Carter | 623/52 |
| 2,470,480 | 5/1949 | Fogg . | |
| 2,475,372 | 7/1949 | Cantranis . | |
| 2,475,373 | 7/1949 | Catranis . | |
| 2,605,475 | 8/1952 | Burger . | |
| 2,619,652 | 12/1952 | Vesper . | |
| 2,749,557 | 6/1956 | Riddle . | |
| 3,551,914 | 1/1971 | Woodall . | |
| 3,754,286 | 8/1973 | Ryan . | |
| 3,920,610 | 11/1975 | Wagner . | |
| 4,306,320 | 12/1981 | Delp . | |
| 4,328,594 | 5/1982 | Campbell . | |
| 4,364,128 | 12/1982 | Mummert . | |
| 4,446,580 | 5/1984 | Furuya . | |
| 4,506,395 | 5/1985 | Haiipt . | |
| 4,547,913 | 10/1985 | Phillips | 623/27 |
| 4,636,220 | 1/1987 | Ziegelmeyer | 623/53 |
| 4,645,509 | 2/1987 | Poggi | 623/53 |
| 4,650,492 | 3/1987 | Barkhorder et al. | 623/24 |
| 4,718,913 | 1/1988 | Voisin | 623/49 |
| 4,721,510 | 1/1988 | Cooper | 623/55 |
| 4,770,662 | 9/1988 | Gianpapa | 623/24 |
| 4,808,187 | 2/1989 | Patterson et al. | 623/25 |
| 4,822,363 | 4/1989 | Phillips | 623/27 |
| 4,865,612 | 9/1989 | Arbogast | 623/55 |
| 4,892,553 | 1/1990 | Prahl | 623/55 |
| 4,892,554 | 1/1990 | Robinson | 623/55 |
| 4,959,073 | 9/1990 | Merlette | 623/55 |
| 5,037,444 | 8/1991 | Phillips | 623/53 |
| 5,062,859 | 11/1991 | Naeder | 623/53 |
| 5,066,305 | 11/1991 | Firth | 623/53 |
| 5,112,356 | 5/1992 | Harris | 623/49 |
| 5,116,383 | 5/1992 | Shorter | 623/49 |
| 5,116,384 | 5/1992 | Wilson | 623/49 |
| 5,139,525 | 8/1992 | Krisltinsson | 623/50 |
| 5,246,463 | 9/1993 | Gianpapa | 623/24 |

FOREIGN PATENT DOCUMENTS

| | | | |
|---|---|---|---|
| 058391 | 1/1925 | France | 623/53 |
| 2626463 | 8/1989 | France | 623/53 |
| 0295807 | 12/1916 | Germany | 623/55 |
| 0325171 | 9/1920 | Germany | 623/53 |

OTHER PUBLICATIONS

"The Seattle Lightfoot" marketing brochure.
"The New Modular-III Flex-Foot and Flex-Walk II" marketing brochure.
"Carbon Copy System III" marketing brochure.

*Primary Examiner*—David H. Willse
*Attorney, Agent, or Firm*—Jon C. Christiansen; Daniel P. McCarthy

[57] ABSTRACT

A prosthetic foot formed by one continuous coil spring which has a foot center coil section, a heel extension section, and a forefoot extension section. Lateral and medial and torsional movement are accommodated. Energy is absorbed and stored by the prosthetic foot during heel strike in the gait cycle, energy is transferred to the forefoot extension section during foot roll-forward to toe-off in the gait cycle, and energy is released to provide a propelling force on the prosthetic foot at toe-off in the gait cycle. An apparatus allowing the wearer of the prosthetic foot to feel by physical sensation forces being applied to the prosthetic foot is included in one embodiment.

7 Claims, 7 Drawing Sheets

COIL SPRING PROSTHETIC FOOT

I. BACKGROUND OF INVENTION

A. The Field of the Invention

This invention relates to the field of prosthetic foot and leg devices, particularly those providing a springing action, torsional and lateral and medial movement, vertical shock absorption and sensory feedback to help the prosthetic foot approximate the response and performance of a natural foot.

B. The Background Art

Various prosthetic feet in the prior art have been designed with spring components intended to store energy when the foot is placed on the ground and to release it and provide a lift or thrust as the foot is removed from the ground again to aid in the patient's gait. Examples of this are Abrogast et al., U.S. Pat. No. 4,865,612 (Issue Date: Sep. 12, 1989) and Shorter et al., U.S. Pat. No. 5,116,383 (Issue Date: May 26, 1992) which are hereby incorporated by reference. Other prosthetic feet in the prior art have used an ankle joint intended to accommodate terrain and walking conditions. Example of this are Voisin, U.S. Pat. No. 4,718,933 (Issue Date: Jan. 12, 1988) and Delp, U.S. Pat. No. 4,306,320 (Issue Date: Dec. 22, 1981) which are hereby incorporated by reference. Poggi et al., U.S. Pat. No. 4,645,509 (Issue Date: Feb. 24, 1987), which is hereby incorporated by reference, disclosed a prosthetic foot which could accommodate uneven terrain by utilizing separate individual toe portions as part of a monolithic cantilever beam. Other prosthetic feet in the prior art have employed multiple springs, including multiple leaf springs, in an attempt to approximate the response and performance of a natural foot. Examples include Merlette, U.S. Pat. No. 4,959,073 (Issue Date: Sep. 25, 1990); Phillips, U.S. Pat. No. 4,547,913 (Issue Date: Oct. 22, 1985); Phillips, U.S. Pat. No. 4,822,363 (Issue Date: Apr. 18, 1989); and Phillips, U.S. Pat. No. 5,037,444 (Issue Date: Aug. 6, 1991), each of which is hereby incorporated by reference.

No prosthetic foot in the prior art has been completely successful in approximating the performance and response of a natural foot, however. Those prior art prosthetic feet which did not utilize a spring-loaded heel, such as Voisin and Delp, experienced a lag or deadness after the patient placed the heel on the ground and began to roll the foot forward during the gait cycle. This was due to the necessity of loading a spring in the toe section after the patient's weight had been placed on the ground. The response and feel of a natural foot cannot be achieved unless the spring(s) are loaded as the patient's weight is placed on the ground rather than after. Prior art prosthetic feet that utilized a spring-loaded heel which operated on a spring separate from a spring in the toe section, such as the Phillips patents and Merlette, effectively stored energy in the heel, but were ineffective in transferring the energy from the heel to the toe portion of the prosthetic foot as the foot rolled forward during the gait cycle. These devices still required separate loading of a spring in the toe section. As a result, the patient noticed a distinct and unnatural lag or hesitation in rolling the foot forward during the gait cycle, giving the foot an unnatural feel and possibly causing an uneven stride. Another problem with multi-spring or multi-component prosthetic feet is that the fasteners, such as bolts, used to fasten the various components to each other quickly wear the spring material resulting in short useful life. Composite material such as graphite laminate, generally recognized as one of the best materials currently available for manufacture of prosthetic feet, is particularly susceptible to this. Two Phillips patents (U.S. Pat. Nos. 4,822,363 and 5,037,444) illustrate the use of problematic fasteners. Reinforcement of the spring material sufficient to reduce this wear to a tolerable level results in thickening of the spring and loss of its responsiveness. The use of spring steel to construct the prosthetic foot reduces the undesirable wear but provides a heavy prosthesis and quickly becomes brittle and breaks during continuous use. Aluminum can be used to construct a lightweight prosthetic foot, but it has insufficient springiness and resiliency to provide a prosthetic foot which accomplishes the goals of the present invention. Those prior art prosthetic feet which utilized a one-piece spring throughout the foot, such as Shorter et al., experienced a lag or deadness after the patient placed the heel on the ground and began to roll forward because the spring design was not suited to absorb and store sufficient energy in the heel and then transfer it to the toe section, thus requiring the toe section to be loaded after the patient's weight had been placed on the ground. Some prior art prosthetic feet, such as Phillips (U.S. Pat. No. 4,547,913) could accommodate torsional movement about the longitudinal axis of the shin portion, but the shape of the shin portion was designed for spring strength and breaking strength, not torsional movement, and the torsional stiffness of the shin section was not adjustable. Finally, prosthetic feet in the prior art lacked any effective means for absorbing and storing energy when vertical force is applied to the foot. Prior art prosthetic feet which utilized a plurality of springs, such as Phillips, tended to rock under vertical load as the load was distributed separately to the springs. Prior art prosthetic feet with a single spring member and a foam heel tended to absorb vertical load either in the spring member or in the foam heel, but not in both. Thus, the prior art exhibited a need for a prosthetic foot which approximates the performance and response of a natural foot by using a spring-loaded heel section integral with a spring-loaded toe section and capable of transferring energy from the heel to the toe during the gait cycle without lag or hesitation, a one-piece prosthetic foot without fasteners that may wear the spring material, a prosthetic foot that can accommodate angled or uneven terrain, a prosthetic foot capable of accommodating lateral and medial movement, a prosthetic foot capable of accommodating torsional movement about the longitudinal axis of the shin with means for adjusting torsional stiffness and a prosthetic foot capable of evenly absorbing and storing energy when vertical force is applied to the foot.

II. SUMMARY OF THE INVENTION

It is an object of the invention to provide a prosthetic foot which stores energy upon heel strike with weight applied in the gait cycle, transfers energy during foot roll-forward to mid foot (flat foot) and to toe-off in the gait cycle, and releases energy at toe-off to provide a propelling lift or thrust to the prosthetic foot to aid in achieving a natural gait. It is a further object of the invention to provide a prosthetic foot which uses a heel extension section integral with a forefoot extension section and capable of transferring energy from the heel to the forefoot during the gait cycle without lag or hesitation. It is a further object of the invention to provide a one-piece prosthetic foot in the form of a continuous coil spring that will eliminate the need for fasteners that may cause wear to the spring material. It is a further object of the invention to provide a prosthetic foot which has a plurality of toe and heel extensions which can accommodate uneven or angled terrain. It is a further object of the invention to provide a prosthetic foot which can accommodate angled or uneven terrain without the use of an ankle joint. It is a further object of the invention to provide a prosthetic foot which utilizes a single continuous coil spring design having either single or a plurality of toe and heel extensions. It is a further object of the invention to provide a prosthetic foot which can accommodate lateral and medial movement by use of toe and heel extensions. It is a further object of the invention to provide a prosthetic foot which includes a mechanism for adjusting spring stiffness. It is a further object of the invention to provide a prosthetic foot capable of torsional movement about the longitudinal axis of the shin with optional means for torsional stiffness adjustment. It is a further object of the invention to provide a prosthetic foot which has high spring strength. It is a further object of the invention to provide a prosthetic foot which has high breaking strength. It is a further object of the invention to provide a prosthetic foot which approximates the performance and response of a natural foot. Further objects and advantages of the invention will become apparent to those skilled in the art.

IV. DETAILED DESCRIPTION OF THE PREFERRED EMBODIMENT

Figure 1:
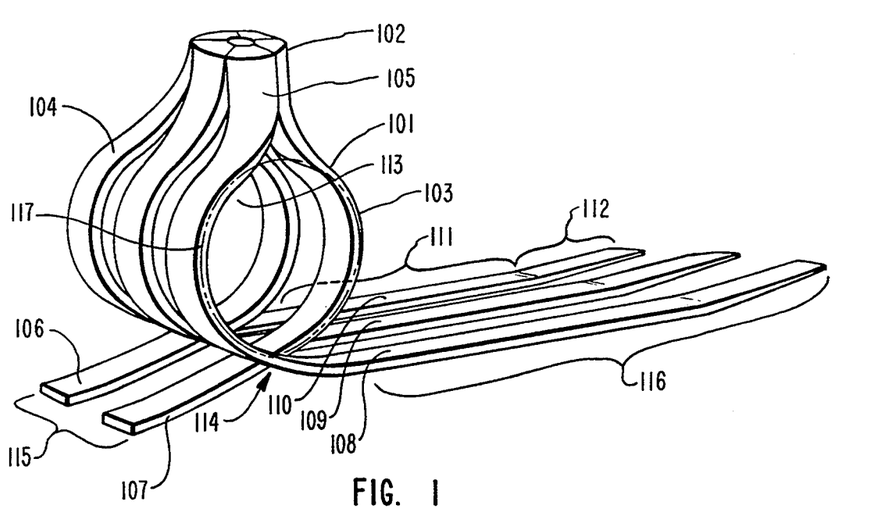
FIG. 1 depicts a perspective view of one embodiment of the invention.

Referring to FIG. 1, a perspective view of one preferred embodiment of the invention is depicted. Shown is a prosthetic foot 101 including shin section 102, anterior coil spring section 103, posterior coil spring section 104, torsional beams 105, lateral posterior heel extension 106, medial posterior heel extension 107, medial anterior toe extension 108, mid anterior toe extension 109, lateral anterior toe extension 110, rear toe portions 111, fore toe portions 112, receptacle 113 to accommodate an optional means for adjusting spring stiffness and arch height (not shown in this figure), and arch 114. Fore toe portions 112 are situated at an angle to rear toe portions 111 so that the fore toe portions 112 extend upward when the foot 101 is resting on the ground. A cut-away of shin section 102 revealing the shape of the torsional beams 105 in cross section is also depicted.

The toe portions 111 and 112 comprise the forefoot extension section 116. Each portion of the forefoot extension section 116 (i.e. 108, 109, 110, 111, and 112) is chosen of a length to approximate not only the size and contour of a natural foot, but also the performance characteristics of a natural foot. The heel extensions 106 and 107 comprise a heel extension section 115. About the receptacle 113 is found the foot center coil 117 (as indicated by the dashed line) which is the central and strongest part of the continuous coil spring which makes up the foot. Heel extension section 115, forefoot extension section 116, the shin section 102, and all constituent members thereof are extensions extending from the foot center coil 117. In this embodiment, the shin section 102 is composed of five (5) torsional beams 105 as shown by the cut-away. Each torsional beam 105 extends from the anterior or posterior coil sections 103 and 104 which are provided by curvature of the toe extensions 108, 109 and 110, and the heel extensions 106 and 107 as they arc through the foot center coil section 117 and coil spring sections 103 and 104 and then upwards to form the shin section 102. The torsional beams 105 allow torsional movement about the longitudinal axis of the shin 102. This torsional movement complements the lateral and medial flexibility of the prosthetic foot 101 provided by the individual toe and heel extensions 108, 109, 110, 106, and 107.

The individual toe and heel extensions 108, 109, 110, 106, and 107 permit lateral and medial movement of the foot to accommodate uneven or angled terrain without the necessity of an ankle joint. The number of toe and heel extensions varies from one each up in different embodiments, although a plurality is preferred. In this embodiment, the shape and joining of the various spring members comprise the foot as one coil spring with the foot center coil 117 at the center and heel extension section 115, forefoot extension section 116, and shin section 102 extending from and connected to the foot center coil section 119. In other embodiments, the prosthetic foot 101 may be composed of a continuous coil spring which includes toe and heel extensions. The prosthetic foot 101 may also be composed of various spring sections fastened to each other to form a coil spring. Non-spring sections may be incorporated as well, provided that those sections located in positions where a transfer of stored energy is necessary to achieve the goals of the invention are capable of such energy transfer. If the prosthetic foot 101 is formed of various sections, then those sections may be fastened to each other by the use of clamps, bolts, screws, chemical bonding such as adhesive or epoxy, welding or otherwise. One key characteristic of the foot center coil section 119 is that it has the ability to transfer energy from heel to toe during foot roll-forward in the gait cycle. A prosthetic foot in the form of a coil spring is chosen because it has this characteristic. Foot center coil section 117 may also have the ability to absorb shock or energy as vertical force is applied to the foot.

The ability to store and release such energy are also desired characteristics of foot center coil section 117. The foot center coil section 117 includes a void within its interior surface. The interior surface of foot center coil section 117 may be a closed plane curve, and the points along the curve (i.e. along coil sections 103 and 104) may be equidistant from the center of a closed plane to form a circle or they may be of varying distances from the center to form other shapes. Alternatively, the interior surface of the foot center coil section 117 may be formed by two arcs such as coil spring sections 103 and 104 such that the foot center coil section 117 lacks a continuous and uninterrupted interior surface but forms the general shape of a circle or oval within its interior.

In the preferred embodiment, the interior surface of the foot center coil section 117 is oval in shape. The exact size and shape of the foot center coil 117 depends on the size, weight and activity characteristics of the patient who is to wear the prosthetic foot 101. Varying size, shape, contour, strength, materials and other characteristics of foot center coil 117 yields different spring characteristics and energy transfer abilities. The void formed by the curvature of the coil sections 103 and 104 within the foot center coil 117 serves as a receptacle 113 for an optional means for adjusting spring stiffness and arch height. The adjustment may be used to vary spring stiffness and/or arch height 114. Inclusion of a shin 102 makes this embodiment of the invention suitable for a patient who had an amputation at some point above the ankle. Omission of the shin section 102 would make the prosthetic foot 101 suitable for a patient who has had an amputation at a lower point on the leg or otherwise does not require the shin. Each toe and heel extension section and each torsional beam may be of a different strength and of varying thickness along their length to possess characteristics as similar as possible to a natural foot. This produces a differential in spring stiffness. Variation in lengths, widths, thicknesses and strength will be necessary depending upon the size, weight, and activity level of the patient.

In alternative embodiments, the toe extensions 108, 109 and 110 may be connected to each other via a strap or cord, as may the heel extensions 106 and 107. When the foot is in use, it is typically encased in a cosmetic footshell resembling a natural foot. The footshell can include bridges or grooves to keep each of the toe extensions and heel extensions separate from the others and in alignment. The aforementioned strap, cord, bridges or grooves all serve as means for maintaining alignment and positioning of toe and heel extensions. Alternatively, the continuous coil spring foot could use a single toe extension and a single heel extension rather than a plurality of toe and heel extensions.

Figure 2:
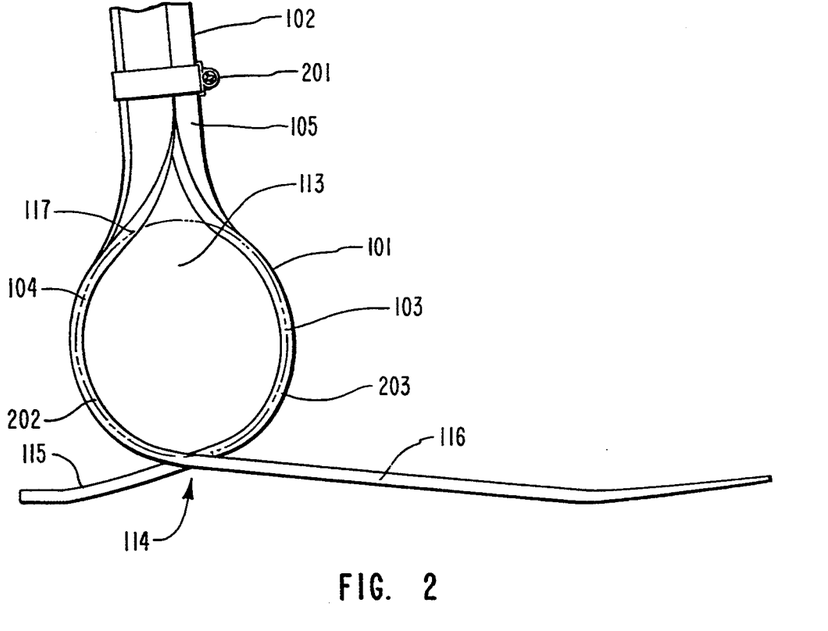
FIG. 2 depicts a side view of one embodiment of the invention.

Referring to FIG. 2, a side view of one embodiment of the invention is shown. The shape of the heel extension section 115, coil spring sections 103 and 104, forefoot extension section 116 and shin section 102 form the foot center coil section 117 and receptacle 113 in a generally oblong or oval shape although an egg shape, circular shape, closed plane curve, arch shape or other shape to embody desired spring and energy transfer characteristics would also be suitable. One or more clamps 201 along the shin 102 may be provided to allow adjustment of torsional stiffness. Tightening clamps 201 restricts movement of the torsional beams 105 and loosening clamps 201 permits greater movement of the torsional beams 105, allowing the patient to adjust torsional stiffness as needed, depending on the activity and terrain. These clamps 201 or other similar device serve as a means for adjusting torsional stiffness. Such adjustment means could include any device capable of restricting movement of the torsional beams 105.

In FIG. 2, the invention may also be described as a plurality of arched or curved spring means 202 and 203 oriented in an overlapping and opposite fashion. A central receptacle 113 is formed by a combination of the arched shape of the spring means and the orientation of some of the spring means opposite others. In the figure, arched spring means 202 is oriented opposite and overlapping arched spring means 203 to form a central receptacle 113. An arched heel spring means 203 is employed which includes a heel extension 115, an anterior coil spring section 103, and a torsional beam 105. An arched forefoot spring means 202 is employed which includes a forefoot extension 116, a posterior coil spring section 104, and a torsional beam 105. The anterior and posterior coil springs 103 and 104 are arched. Through the use of shape of arched spring means 202 and 203 and appropriate materials, resilient, flexible and durable arched spring means 202 and 203 with spring-like qualities are achieved. The orientation and overlap of arched spring means 202 and 203 form a foot center coil section 117 when the arched spring means 202 and 203 are assembled to form a prosthetic foot 101. An arch 114 may also be included. Within foot center coil section 117, the receptacle 113 serves a receptacle for accommodating an optional means for adjusting spring stiffness and arch height. In a preferred embodiment of the invention, arched spring means 202 and 203 are individually removable and replaceable in the aftermarket by the wearer or a service technician. Any retaining mechanism would be released to allow removal of an arched spring means. Once an arched spring means is removed, another of different size and/or strength characteristics would be installed in the prosthetic foot. This allows aftermarket selection of arched spring means 202 and 203 of differential spring strengths to achieve lateral and medial adjustability of the prosthetic foot. In this manner, each toe and heel extension may be of a different size and strength as appropriate for the particular patient. Through this selection of spring means 202 and 203, a lateral and medial spring strength differential across toe extension sections 108, 109 and 110 and across heel extension sections 106 and 107 can be achieved. Worn or broken parts of the prosthetic foot may be replaced in the same manner. The ability to replace spring means to achieve a spring strength differential is referred to as a means for achieving a lateral and medial spring strength differential in the prosthetic foot 101.

Figure 3:
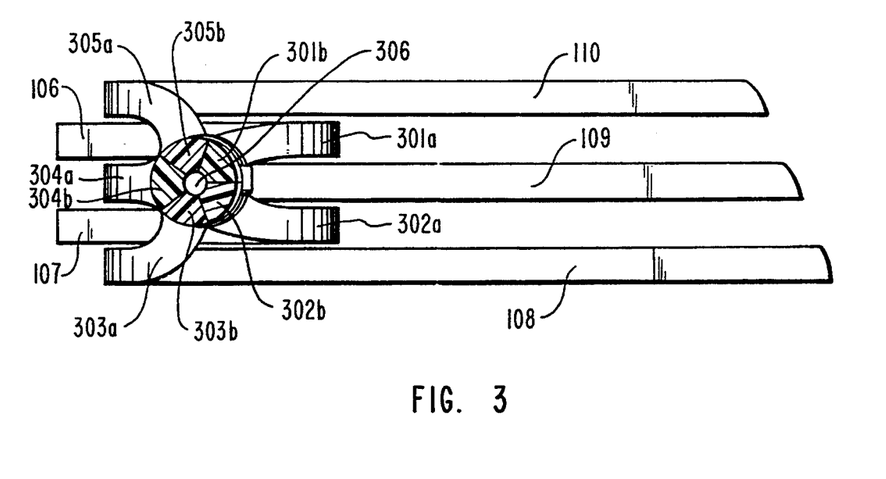
FIG. 3 depicts a top view of one embodiment of the invention.

Referring to FIG. 3, a top view of a preferred embodiment of the invention is shown. This figure depicts the shape and curvature of the various spring sections which form the prosthetic foot 101 in a large continuous coil. Lateral posterior heel extension 106 curves through its anterior coil section 301a to become a torsional beam 301b. Medial posterior heel extension 107 curves through its anterior coil section 302a to become a torsional beam 302b. The toe extensions are similarly designed. Medial anterior toe extension 108 curves through its posterior coil section 303a to become a torsional beam 303b. Mid anterior toe extension 109 curves through its posterior coil section 304a to become a torsional beam 304b. Finally, medial anterior toe extension 110 curves through its posterior coil section 305a to become a torsional beam 305b. Convergence of the torsional beams 301b, 302b, 303b, 304b and 305b forms the longitudinal or vertical axis 306 of the shin 102. The vertical axis 306 in this embodiment is hollow and is the axis about which the prosthetic foot accommodates torsional movement. Torsional beams 301b, 302b, 303b, 304b, and 305b are pie-shaped in longitudinal cross-section in the preferred embodiment. By using pie-shapes, a shin 102 which is round in longitudinal cross-section and cosmetically appealing is achieved. Equivalent performance characteristics may be achieved with pie beams 105 which are of another shape in longitudinal cross-section, such as square, octagonal, round, or otherwise. The torsional beams 105 serve as means for accommodating torsional movement about a longitudinal axis through the shin section 102. As the foot 101 is twisted about the vertical axis 306, the individual torsional beams 301b, 302b, 303b, 304b, and 305b twist about axis 306 as well to accommodate the torsional movement. In the preferred embodiment, the surfaces of torsional beams 301b, 302b, 303b, 304b, and 305b which contact each other are coated with TEFLON (such as by spraying a TEFLON coating on them or gluing TEFLON sheets to them) or any other friction-reducing substance to allow torsional movement inhibited only by the strength and resiliency of the torsional beams 301b, 302b, 303b, 304b, and 305b and not by friction. Clamps 202 as depicted in FIG. 2 are generally concentric about the axis 306 in the preferred embodiment, although another means for adjusting torsional stiffness may be used which does not include clamps concentric about the axis 306.

In another embodiment, the means for absorbing and storing energy when vertical force is applied to the prosthetic foot is found in the shin 102 rather than or in addition to the arch 114. It includes a center rod running along the axis 306 and rigidly attached to a fitting at the top of the shin, with the torsional beams 301b, 302b, 303b, 304b, and 305b bowed away from the axis 306 and the center rod in the middle of the shin 102. The center rod may be rigid or flexible. The bowing may be slight, such as 0.25". When this absorbing means is employed, vertical force on the prosthetic foot 101 causes the center rod to move downward along the axis 306 and the torsional beams 301b, 302b, 303b, 304b, and 305b to each bow outward as they absorb and store energy. As vertical force on the prosthetic foot 101 is released, the center rod travels upward along the axis 306 and the torsional beams 301b, 302b, 303b, 304b, and 305b return to their original position, releasing their stored energy and providing an upward push or thrust on the patient to aid in gait. The upward thrust or lift aids in gait by providing a foot which uses stored energy to push off as it leaves the ground, as compared to some prosthetic feet in the prior art which were not spring-loaded and could not provide any thrust or lift. The means for adjusting torsional stiffness 201 could be employed in this embodiment, serving not only to adjust torsional stiffness, but also as a means for limiting vertical displacement of the shin section 102 by limiting the amount of outward bow which the torsional beams 301b, 302b, 303b, 304b, and 305b can achieve. This would effectively stiffen the vertical shock absorption characteristic of the shin as well as stiffening the torsional movement means.

Figure 4A:
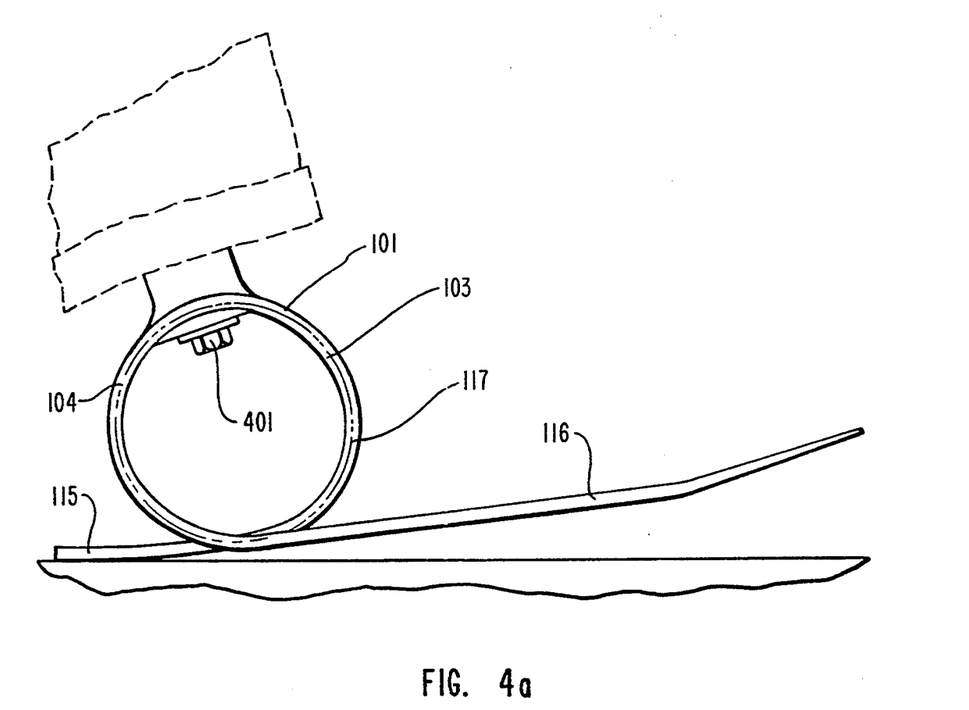
FIG. 4a depicts heel strike with weight applied in the gait cycle of one embodiment of the invention in walking or running use.

Referring to FIG. 4a, heel strike with weight applied in the gait cycle of one embodiment of the invention in walking or running use is depicted. The gait cycle is the sequence of movements which a foot goes through from heel strike to mid foot to toe-off during normal walking, running, or jumping use. As the heel extension section 115 of the foot 101 is set onto the ground and weight applied to it, the posterior heel extensions 106 and 107 are compressed and loaded and store energy along their length and in the anterior coil spring section 103 of foot center coil section 117. The heel extension section 115 along with anterior coil spring section 103 of foot center coil section 117 comprise a means for absorbing and storing energy at heel strike during the gait cycle. At this point in the gait cycle, the forefoot extension section 116 of the foot 101 has not yet contacted the ground. In the embodiment of the invention depicted in FIG. 4a, the shin section 102 and torsional beams 105 are omitted, and a nut 401 for attaching the foot 101 to a fixture on an ankle suited to receiving a prosthetic foot is provided. This allows the foot 101 to be used by patients who do not require shin portion 102.

Figure 4B:
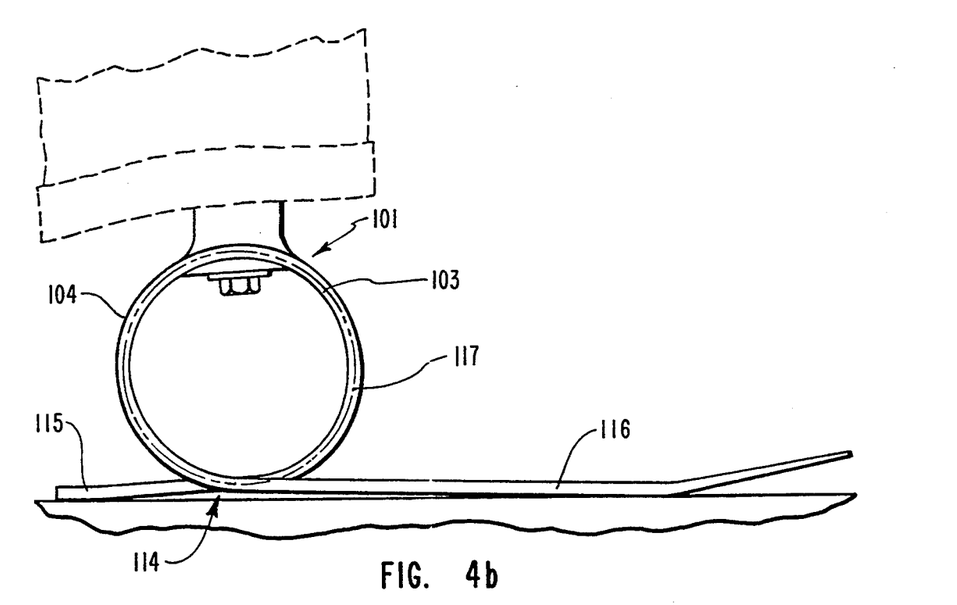
FIG. 4b depicts mid foot (flat foot) in the gait cycle of one embodiment of the invention in walking or running use.

Referring to FIG. 4b, mid foot (flat foot) in the gait cycle of one embodiment of the invention in walking or running use is depicted. This point in the gait cycle occurs as the foot rolls from heel strike forward along the ground. In this figure, the forefoot extension section 116 and the heel extension section 115 are in contact with the ground and are compressed or loaded under the weight of the patient's body. The arch 114 is similarly compressed. At this point, energy is stored by the forefoot extension section 116, the heel extension section 115, the arch 114, and coil spring sections 103 and 104 of the foot center coil section 117. As the foot rolls forward toward toe-off, energy is transferred from the heel extension section 115 and the arch 114 through the foot center coil section 117 into the forefoot extension section 116 resulting in a smooth and uninterrupted foot action through the gait cycle. The foot center coil section 117, in conjunction with heel extension section 115 and toe extension section 116 serves as a means for transferring energy from heel section to forefoot section in the foot 101. Because the entire foot 101 is a coil spring, no energy is lost or separate loading of different spring members required which would result in hesitation, lag or unevenness in the gait.

FIG. 4b also depicts the position of the foot 101 when the patient applies vertical force to it directly from above, such when landing on the ground after jumping vertically. Forefoot extension section 116, heel extension section 115, foot center coil section 117 and arch 114 are compressed and loaded as the patient's weight is applied to the foot 101. The arch 114 in conjunction with the forefoot extension section 116, heel extension section 115 and foot center coil 117 serve as means for absorbing and storing energy when vertical force is applied to the prosthetic foot 101.

Figure 4C:
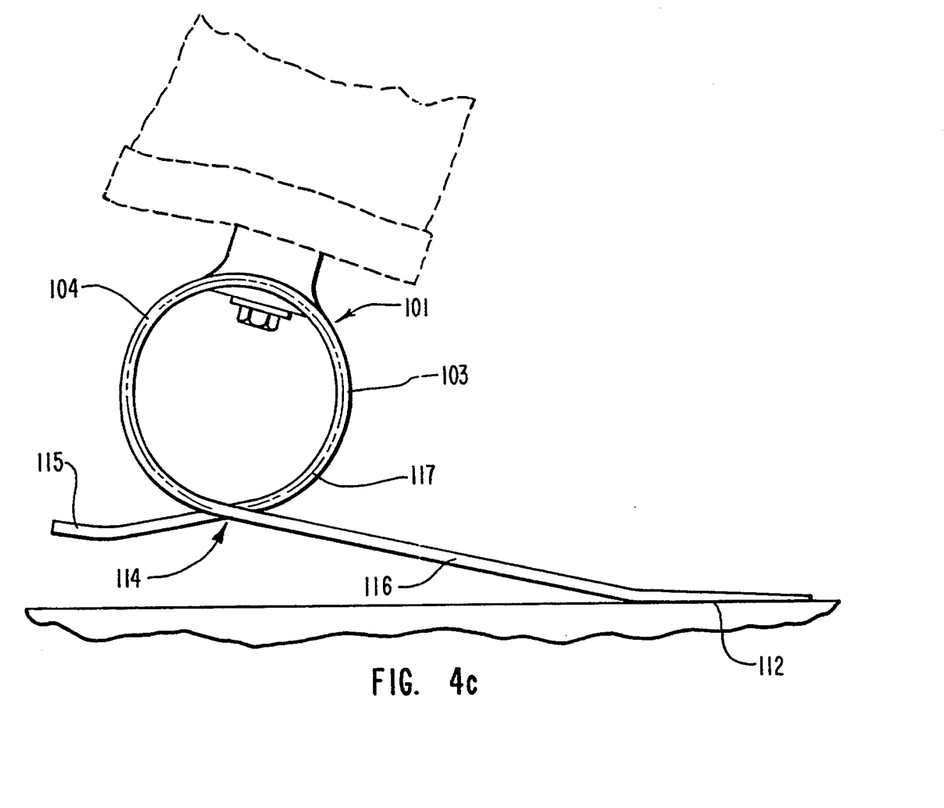
FIG. 4c depicts toe off in the gait cycle of one embodiment of the invention in walking or running use.

Referring to FIG. 4c, toe-off in the gait cycle of one embodiment of the invention in walking or running use is depicted. The heel extension section 115 is no longer in contact with the ground and it along with anterior coil spring section 103 have transferred their energy into the forefoot extension section 116 and the posterior coil spring section 104 through the foot center coil section 117. As the foot 101 continues to roll forward and lose contact with the ground, energy stored in the foot center coil section 117 is transferred into the forefoot extension section 116. As the foot 101 completes the gait cycle, fore toe portions 112 are the last portion of the foot 101 to be in contact with the ground, and through the forefoot extension section 116 and constituent fore toe portions 112, energy stored in and transferred through the various portions of the foot 101 is released to provide a gait-enhancing propelling force such as a spring or a thrust on the foot 101 to aid in achieving a natural gait. This is in contrast with the inert feel of a non-spring loaded foot as it completes the gait cycle. The forefoot extension section 116 in conjunction with the foot center coil 117, particularly posterior coil section 104, serves as a means for propelling the foot 101 forward during toe-off in the gait cycle.

Figure 5:
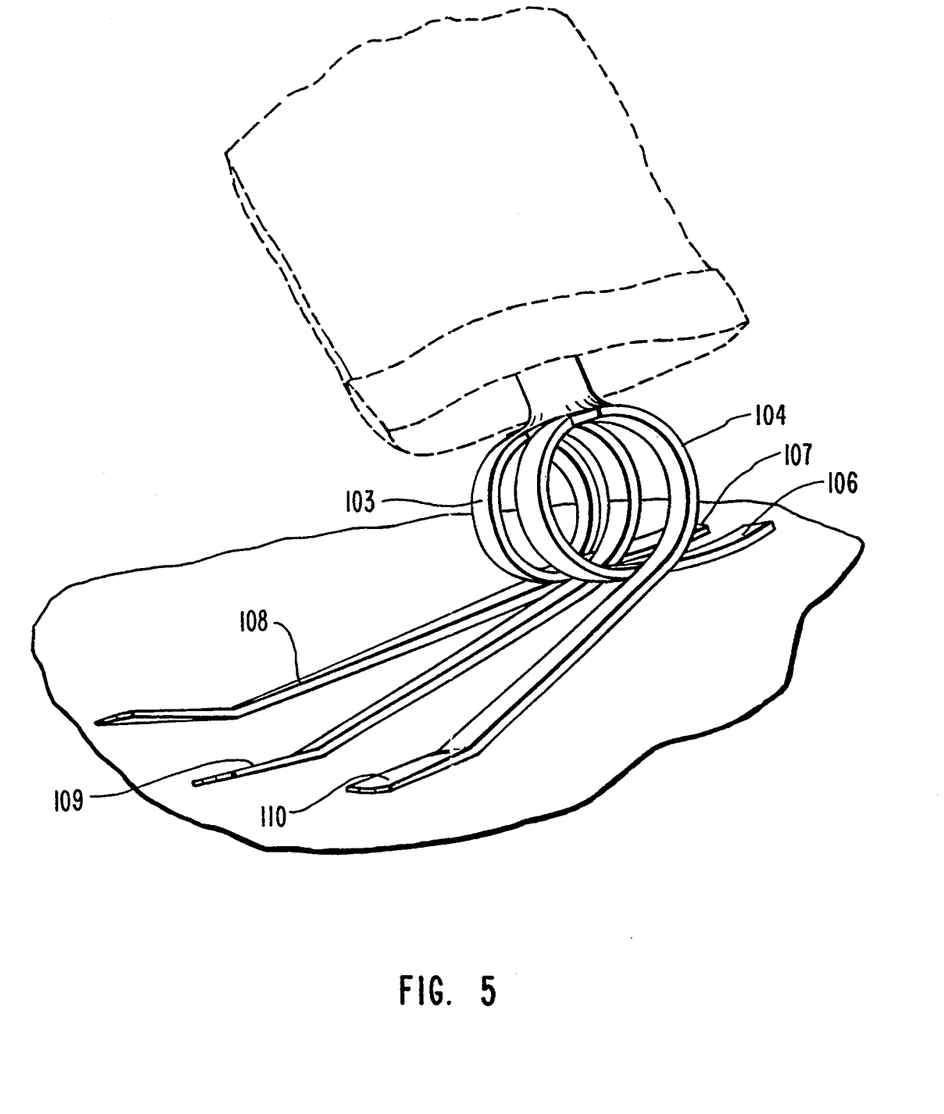
FIG. 5 depicts an action illustration of one embodiment of the invention under lateral and medial load.

Referring to FIG. 5, an action illustration of one embodiment of the invention under lateral and medial load is depicted. This illustrates the ability of the toe sections 108, 109 and 110 and heel sections 106 and 107 to separately conform to and accommodate uneven or angled terrain without the use of an ankle joint. Each toe extension 108, 109 and 110 and each heel extension 106 and 107 is separately loaded according to the demands of the terrain and angle of the shin 102 with the ground. Energy is stored in each of these springs as well as in the anterior and posterior coil spring sections 103 and 104 according to the angle, terrain, and load applied. In this manner, lateral and medial movement is accommodated by the invention and the need for a jointed ankle portion of the prosthetic foot is eliminated. The toe extensions 108, 109 and 110 and the heel extensions 106 and 107 comprise means for accommodating lateral and medial movement of the prosthetic foot 101 without the use of an ankle joint. Simultaneous torsional movement about the longitudinal axis 306 of the shin 102 as well as foot roll-forward during the gait cycle are also possible because the prosthetic foot 101 can accommodate all of these movements simultaneously without lag or hesitation through the use of a coil spring. In this way, the response and performance of a natural foot are approximated.

Figure 6A:
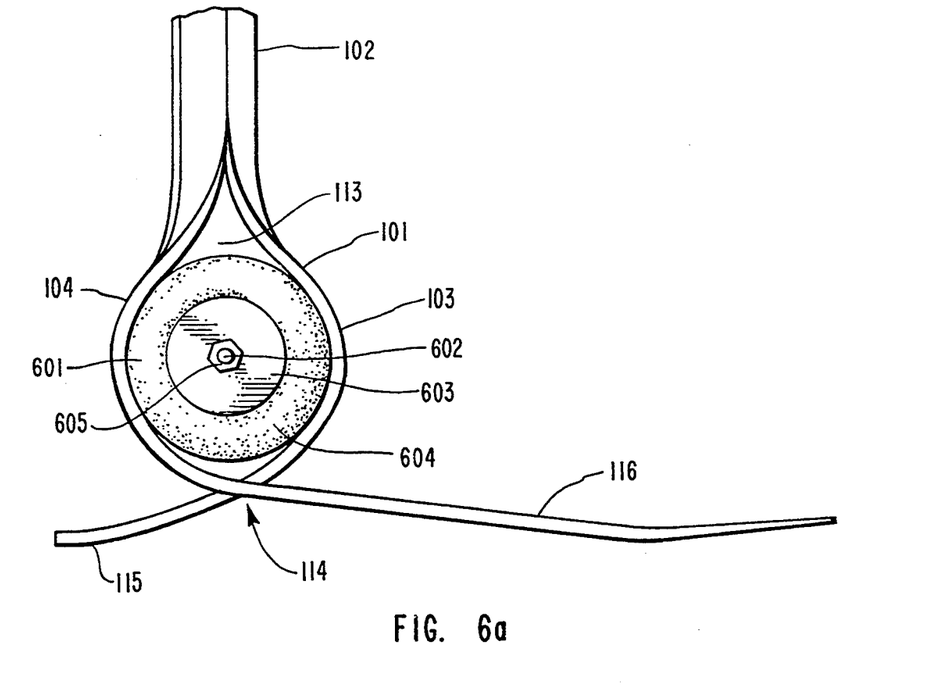
FIG. 6a depicts a side view of one embodiment of the invention with an optional means for adjusting spring stiffness and arch height installed.
Figure 6B:
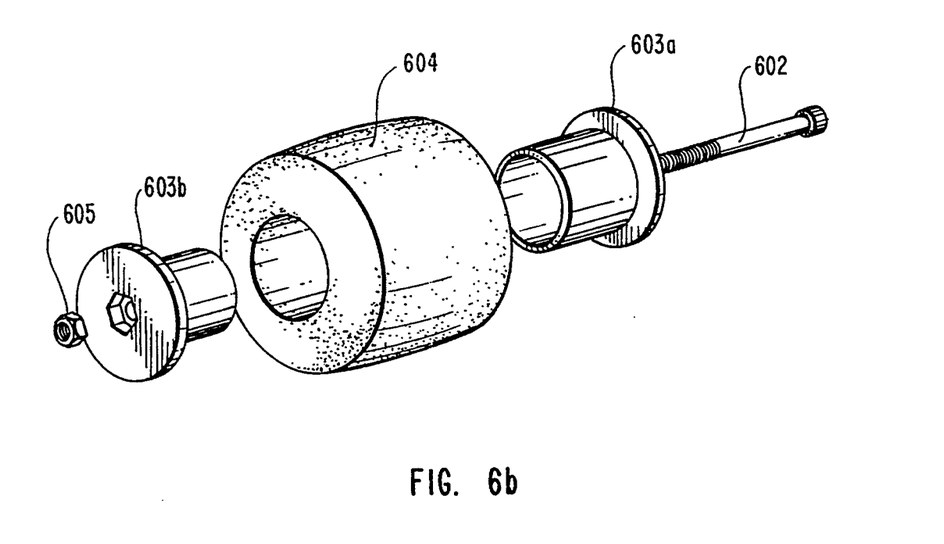
FIG. 6b depicts a parts explosion of one embodiment of an optional means for adjusting spring stiffness and arch height for use with the invention.

Referring to FIG. 6a, one embodiment of the invention which includes a means for adjusting spring stiffness and arch height 601 is depicted. As shown, installed within the receptacle 113 is a cylindrical urethane or foam rubber pad 604 secured by a fitting 603 at each end and a bolt 602 and nut 605. FIG. 6b shows the various components of one embodiment of a means for adjusting spring stiffness and arch height 601 for use with the invention. The cylindrical rubber pad 604 is approximately the same diameter as the interior of the receptacle 113. The interior of the pad 604 has hole to accommodate the fittings 603 and a bolt 602 protruding through it to attach to a nut 605 on the other side. The bolt 602 and nut 605 may be tightened to apply pressure to fittings 603a and 603b. As the fittings 603a and 603b approach each other, their lips compress the pad 604 and cause it to apply outward pressure within the receptacle 113 on coil sections 103 and 104. This outward pressure stiffens coil sections 103 and 104 and lifts the arch 114 to provide greater vertical and roll-forward support and spring stiffness for a heavier or more active patient. In the preferred embodiment, rubber pad 604 is manufactured from urethane rubber, although foam rubber, resilient materials of another type, or other devices to apply outward pressure or force within the receptacle 113 could be employed. Aftermarket pads 604 would be available in different densities to provide different adjusting characteristics for different patients and different activity levels. Various other means for applying pressure to or supporting various spring sections may be used as means for adjusting spring stiffness and arch height as well. For example, a coil spring oriented vertically could be installed in the receptacle 113 to add stiffness or strength to the prosthetic foot. Although no adjustment would be available in that example, it would still be considered a means for adjusting spring stiffness and arch height because it could be installed to increase spring stiffness and arch height, or removed to achieve a lesser spring stiffness and arch height. Because the means for adjusting spring stiffness and arch height affects firmness of the heel extensions at heel strike, transfer of energy during foot roll-forward, and energy release at toe-off in the gait cycle, it is also considered a means for adjusting firmness of energy absorbing, storing, transferring and releasing means.

In another embodiment, an apparatus which communicates a sense of feeling in the foot to the wearer is included. The apparatus includes means for measuring bending and twisting of various parts of the prosthetic foot and means for communicating signals representing those measurement to the wearer of the prosthetic foot so that the wearer can feel by physical sensation the position of the foot. The measuring means would measure such quantities as forefoot extension bend and torsional beam twist, among others. For the purposes of the invention, the term "bend" shall also mean "twist." The preferred means for measuring bending of various parts of the foot includes strain gauges on the forefoot extension section, heel extension section, foot center coil, shin section, and their various sub-components. A subset of these and/or others may also be used as well. The use of strain gauges is well-known in the prior art for measuring such things as I-beam movement in buildings. In the invention, strain gauges measure the amount of bending occurring at various points on the foot regardless of the amount of load being applied. Readings from the strain gauges are then communicated by signals to a section of skin on the patient's body, such as by electrical currents, mechanical pressure, or sonic vibrations to allow the patient to feel by physical sensation the position, angle, and bending of various parts of the foot. Signal strength, intensity or amplitude (hereinafter jointly referred to as "amplitude") transmitted to the patient's skin indicate the amount of bending occurring at various points on the foot. The section of skin used would typically be somewhere in the patient's leg or calf, and the patient would learn the meaning of various signals by experience until a feedback system keeping the patient informed of the position, angle and bending of the foot similar to that in a natural foot is established. Standard digital electronics or analog circuitry may be used. A microprocessor may be employed to read signals from the strain gauges and determine appropriate output(s) to inform the patient of the angle, position and bending of the various parts of the foot rather than communicating signals directly from the strain gauges to the patient's skin. Alternatively, pressure sensors could be used in lieu of strain gauges to sense the amount of load being applied to various parts of the foot, and all information communicated to the patient would pertain to the amount of load on various portions of the foot rather than the amount of bending of various portions of the foot.

Figure 7:
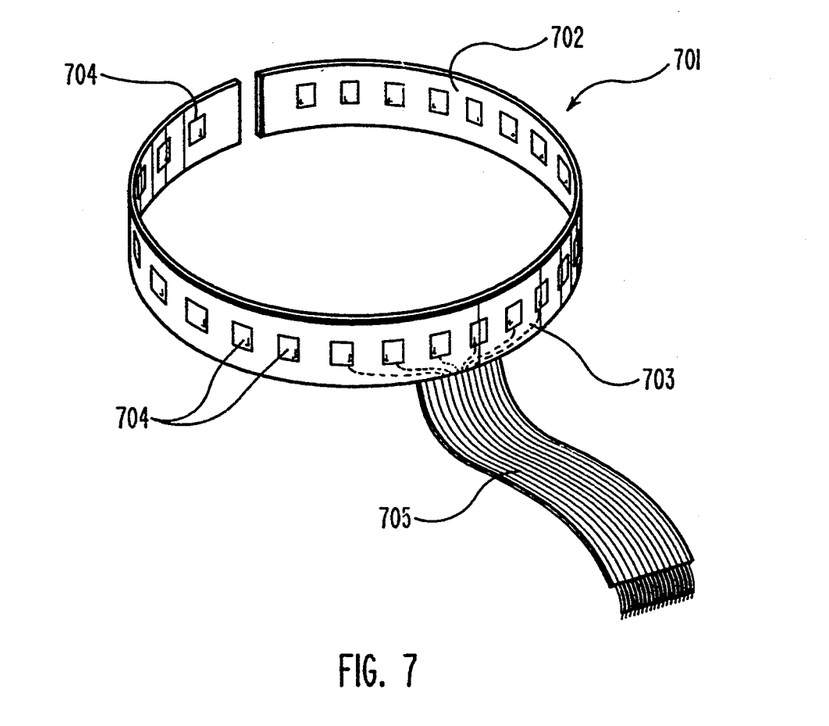
FIG. 7 depicts a sensory feedback band for use in one embodiment of the invention.

FIG. 7 depicts a sensory feedback band 701 which is used as a means for communicating signals representing measurements of bending and twisting of various parts of the prosthetic foot to the wearer of the prosthetic foot so that the wearer can feel by physical sensation the position of the foot. The sensory feedback band 701 depicted is used in the embodiment of the invention which communicates signals to the wearer via electrical current. The sensory feedback band 701 includes inner band surface 702, outer band surface 703, conductive patches 704, and an electrical cable 705. The inner and outer band surfaces 702 and 703 are non-conductive in the preferred embodiment, and outer band surface 703 is typically covered with a fabric such as cotton cloth for protection and cosmetic appeal. Conductive patches 704 may be manufactured from any conductive material known to be capable of conducting electricity to human skin. A plurality of small conductive patches 704 is used in the preferred embodiment. The conductive patches serve as means for communicating signals to the wearer's skin. Electrical cable 705 carries within it a plurality of wires connected to the various conductive patches 704. In the preferred embodiment the cable 705 is flexible, although it may be rigid in some embodiments. It is also possible to mold the cable into a cosmesis covering the prosthetic foot. See FIG. 8 for a diagram of the invention in use. The wires within cable 705 may receive signals from a microprocessor 802 or directly from strain or pressure gauges 801*a–e,* and they transmit the signals to the wearer's skin. In other embodiments of the invention, conductive patches 704 could be replaced by means for applying mechanical pressure to the skin or means for exposing the skin to sonic vibrations. In any of these cases, a portion of the wearer's skin will feel a physical sensation indicating bending of various portions of the prosthetic foot.

It is desirable to place the sensory feedback band 701 at the same position on the wearer's leg each time it is worn. This may be accomplished by molding the sensory feedback band 701 into a cosmesis attachable to the prosthetic foot. Alternative means for accurately locating the sensory feedback band 701 on the wearer's leg may be used. Alternatively, the sensory feedback band 701 may simply be taped, strapped or otherwise affixed to the wearer's leg.

Typically, three sensory feedback bands 701 are employed in the invention, each at a different location on the wearer's leg. This allows signals to be transmitted to the wearer of the prosthetic foot which represent angle, position, bending or twisting of the prosthetic foot. For example, as the strain gauges measure a twisting of the prosthetic foot from left to right, the sensory feedback bands 701, through the conductive patches 704, would transmit signals to the wearer's skin which are of increasing amplitude circumferentially from left to right to correspond to the twisting. As another example, when the prosthetic foot is flat on the ground and the shin bends forward towards the foot, the upper sensory feedback band would communicate signals of greater amplitude to the wearer's skin indicating the increased load on the toe extensions of the foot. And when the prosthetic foot is angled in one direction to accommodate angled terrain, the conductive patches corresponding to those portions of the foot experiencing more bending will communicate a stronger signal to the wearer's leg, indicating that bending. Thus, the invention allows the wearer to feel three-dimensional twisting, bending, anterior, posterior, lateral and medial movement and uneven or angled surfaces which the prosthetic foot may encounter.

Figure 8:
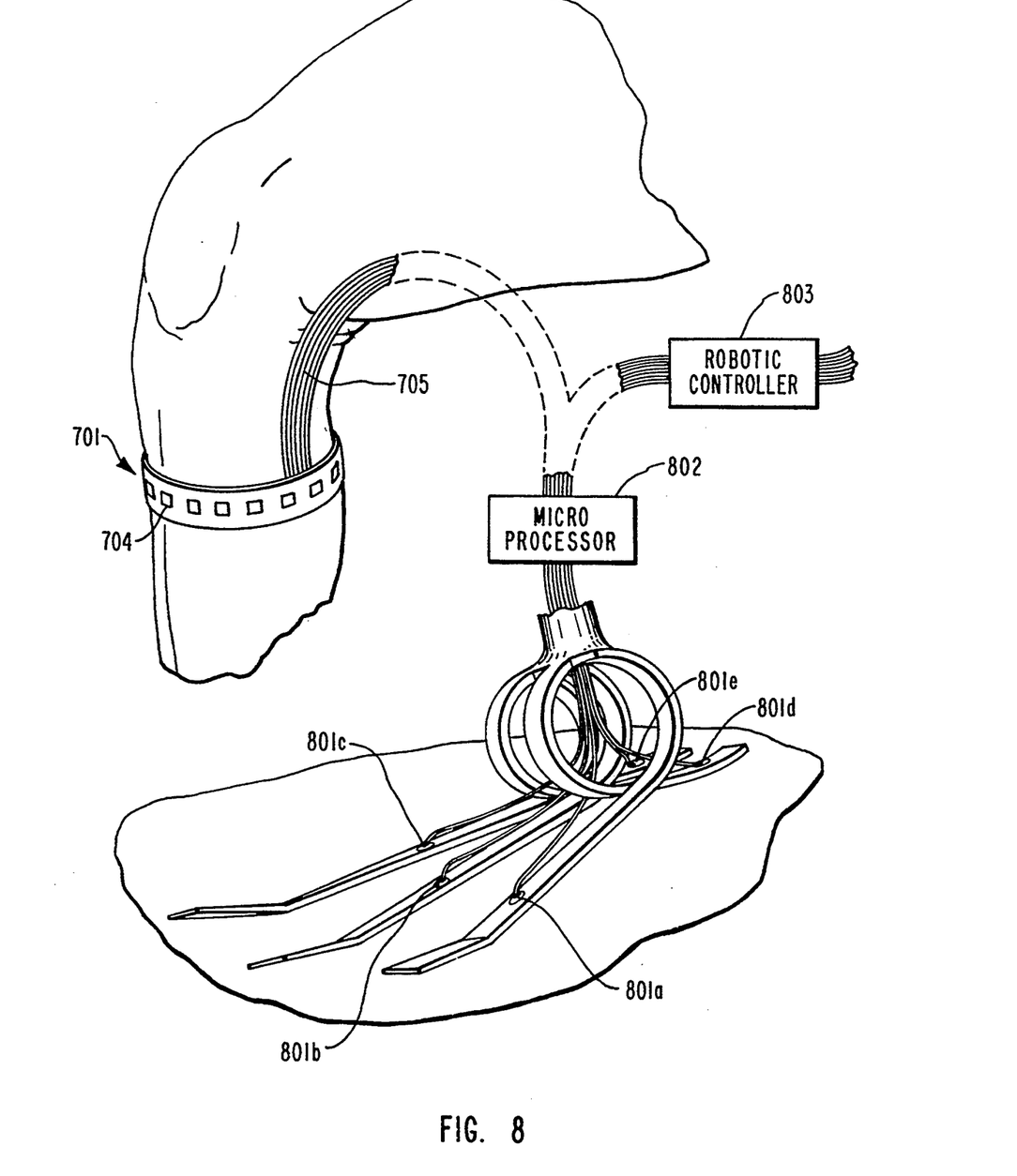
FIG. 8 depicts interconnection and operation of the prosthetic foot, microprocessor, robotic controller and sensory feedback band.

The prosthetic foot including means for measuring bending and twisting of various parts of the prosthetic foot and means for communicating signals representing those measurement to the wearer of the prosthetic foot are also applicable to the field of robotics. If used in robotics, the invention would be referred to as an artificial foot, not a prosthetic foot. Structure and design of the foot could be essentially the same for use in robotics, except that sensory feedback bands 701 would be omitted and all feedback would be routed to a computer system controlling the robotic device 803. One advantage of using the invention as an artificial foot in the field of robotics is that the robotic device need only control the leg onto which the artificial foot attaches, it need not use a foot equipped with the expensive control and measurement apparatus which would be required if a robotic foot with expensive internal motors were employed. The need to control only a robotic leg when the invention is used, and not a robotic foot as well reduces the complexity of control and hence requires a less powerful and less expensive robotic controller due to the lesser computational complexity of controlling simply a leg as compared to controlling a leg and a foot with multiple moveable parts. Although precise foot placement could be achieved when the invention is used, the invention is especially attractive in applications where the primary requirement is foot.

Various materials may be suitable for construction of the prosthetic foot. Graphite fiber, a graphite and fiberglass combination, SPECTRA, KEVLAR or other fiber material impregnated with a resin such as epoxy or polyester resin are all suitable. Both Hercules and Newport Composites provide fabric pre-coated with a resin which may be used in foot assembly and then cured either by baking or chemically, as appropriate. In the preferred embodiment of my invention, graphite fiber fabric impregnated with epoxy resin is used, although other material may be equally suitable. This provides exceptionally high breaking and spring strength while being very light weight, durable, and long-lasting. Alternatively, the spring members which comprise the foot could be injection molded from delron or nylon with appropriately engineered strengths and thicknesses. Any materials or method of manufacture which provides adequate spring strength, stiffness, flexibility, resiliency, and bend without breaking or wearing quickly under constant use would be suitable. Furthermore, other materials such as plastics, metals, alloys, ceramics, etc., may be developed in the future which provide suitable or preferable characteristics for prosthetic foot construction.

The prosthetic foot must be made with spring strength appropriate for the weight and activity level of the patient who is to wear and use it. Both the breaking strength and the spring strength of the foot may be engineered through proper selection of materials and a determination of the thickness of materials to be used in various portions of the foot. Phillips, U.S. Pat. No. 5,037,444 (Issue Date Aug. 6, 1991), which is hereby incorporated by reference, discloses a method for determining appropriate ply thickness of a prosthetic foot constructed from epoxy-impregnated graphite laminate. It should be noted that the graphite fiber material used to construct the preferred embodiment of the prosthetic foot has strength only along one axis and must therefore be laminated in some type of crosshatched pattern to give strength from various directions. Merlette, U.S. Pat. No. 4,959,073 (Issue Date: Sep. 25, 1990), which is hereby incorporated by reference, describes methods of doing this. Foot length and width are chosen depending upon desired foot size. The number of toe and heel extension sections should be selected to provide the performance characteristics sought by the invention, but not be so numerous and hence so thin as to lack strength and durability. Three toe extension sections and two heel extension sections are used in the preferred embodiment of the invention.

The invention provides a prosthetic foot which stores energy upon heel strike with weight applied in the gait cycle, transfers energy through the foot center coil section to the forefoot extension section during foot roll-forward to mid foot (flat foot) in the gait cycle, and finally releases stored energy to provide a propelling force to the prosthetic foot at toe-off in the gait cycle. The invention eliminates any deadness or hesitation when the heel is placed on the ground and any lag or hesitation during foot roll-forward because the entire foot comprises one coil spring with protruding spring members forming forefoot, heel and shin sections. The preferred embodiment of the invention has a plurality of toe and heel extension sections which readily accommodate uneven or angled terrain. Another embodiment of the invention has single toe and heel extension sections which exhibit the same performance characteristics as the preferred embodiment but also easily accommodate uneven terrain. The preferred embodiment of the invention also accommodates angled or uneven terrain without the use of an ankle joint by using multiple toe and heel extension sections which can individually flex to conform to the terrain. Lateral and medial movement is accommodated by the individual toe and heel extension sections and torsional movement is accommodated by multiple torsional beams centered about the longitudinal axis of the shin. Each of the spring sections curves into a foot center coil. The foot center coil section has within it a receptacle which can accommodate a means for adjusting spring stiffness and arch height. A sensory feedback system is included to allow the wearer of the prosthetic foot to feel bending and twisting of the prosthetic foot. High spring strength and breaking strength are achieved in the preferred embodiment by the use of laminated graphite composite material impregnated with epoxy resin to construct the prosthetic foot. The prosthetic foot enables a patient to walk, run, play tennis, racquetball, and basketball and engage in other sports and vigorous activities with substantially the same mobility as an individual with a natural foot. Use of the invention in robotic applications is anticipated.

I claim:

1. A foot comprising:
(a) a foot center coil section having a top and a bottom,
(b) a heel extension section extending in a first direction from the bottom of said foot center coil section,
(c) a forefoot extension section extending in a second direction from the bottom of said foot center coil section,
(d) means for absorbing and storing energy when vertical force is applied to the foot,
(f) means for adjusting spring stiffness and arch height; and
(e) a receptacle to accommodate said means for adjusting spring stiffness and arch height, wherein said receptacle is formed by the interior surface of said foot center coil section;
wherein said foot center coil section, said heel extension section, and said forefoot extension section constitute a coil spring to form the foot;
wherein said foot center coil section is adapted to serve as the unitary center of the coil spring in absorbing, storing and releasing energy;
wherein said energy absorbing and storing means comprises an arch; and
wherein said means for adjusting spring stiffness and arch height is installable in said receptacle.

2. A foot comprising:
(a) a foot center coil section having a top and a bottom,
(b) a heel extension section extending in a first direction from the bottom of said foot center coil section,
(c) a forefoot extension section extending in a second direction from the bottom of said foot center coil section,
(d) a shin section which extends from said foot center coil section;
(e) means for accommodating torsional movement about a longitudinal axis through said shin section;
wherein said foot center coil section comprises an anterior coil spring section and a posterior coil spring section and wherein said heel extension section extends from said anterior coil spring section and said forefoot extension section extends from said posterior coil section;
wherein said foot center coil section, heel extension section, and forefoot extension section constitute a coil spring to form the foot;
wherein said foot center coil section is adapted to serve as the unitary center of the coil spring in absorbing, storing and releasing energy;
wherein said torsional movement means comprises a plurality of torsional beams; and
wherein said torsional beams are generally configured as triangles in longitudinal cross section with two generally straight sides and one generally curved side.

3. A foot comprising:
(a) a foot center coil section having a top and a bottom,
(b) a heel extension section extending in a first direction from the bottom of said foot center coil section,
(c) a forefoot extension section extending in a second direction from the bottom of said foot center coil section,
(d) a shin section which extends from said foot center coil section;
(e) means for accommodating torsional movement about a longitudinal axis through said shin section;
wherein said foot center coil section comprises an anterior coil spring section and a posterior coil spring section and wherein said heel extension section extends from said anterior coil spring section and said forefoot extension section extends from said posterior coil section;
wherein said foot center coil section, heel extension section, and forefoot extension section constitute a coil spring to form the foot;
wherein said foot center coil section is adapted to serve as the unitary center of the coil spring in absorbing, storing and releasing energy;
wherein said torsional movement means comprises a plurality of torsional beams; and
wherein said torsional beams extend from said anterior coil spring section and from said posterior coil spring section;

4. A foot comprising:
(a) a foot center coil section having a top and a bottom,
(b) a heel extension section extending in a first direction from the bottom of said foot center coil section,
(c) a forefoot extension section extending in a second direction from the bottom of said foot center coil section; and
(d) means for absorbing and storing energy when vertical force is applied to the foot;
wherein said foot center coil section, heel extension section, and forefoot extension section constitute a coil spring to form the foot;
wherein said heel extension section is adapted to absorb and store energy at heel strike during the gait cycle;
wherein said foot center coil section is adapted to transfer energy stored during heel strike to another portion of the foot during foot roll-forward of the gait cycle;
wherein said forefoot extension section is adapted to release stored energy at toe-off during the gait cycle to provide a gait-enhancing propelling force on the foot;
wherein said energy absorbing means comprises:
(i) a shin section having a longitudinal axis, said shin section being connected to said foot center coil section, said shin section comprising a plurality of torsional beams;
wherein said torsional beams bow outward to absorb and store energy as vertical force is applied to the foot; and
wherein said shin section experiences a vertical displacement along its longitudinal axis as a result of bowing of said torsional beams.

5. A foot as recited in claim 4 wherein said energy absorbing means further comprises:
(ii) a center rod along the longitudinal axis of said shin section about which said torsional beams have the ability to bow.

6. A foot as recited in claim 5 wherein said energy absorbing means further comprises:
(iii) means for limiting vertical displacement of said shin section.

7. A foot as recited in claim 6 wherein said means for limiting vertical displacement comprises a clamp.

* * * * *